(12) United States Patent
Hause, Jr. et al.

(10) Patent No.: US 8,386,029 B2
(45) Date of Patent: Feb. 26, 2013

(54) APPARATUS FOR ELECTROTHERAPY DRUG DELIVERY WITH ADDED IMPURITIES

(75) Inventors: Robert F. Hause, Jr., Bountiful, UT (US); Jon E. Beck, Salt Lake City, UT (US)

(73) Assignee: Encore Medical Asset Corporation, Henderson, NV (US)

( * ) Notice: Subject to any disclaimer, the term of this patent is extended or adjusted under 35 U.S.C. 154(b) by 615 days.

(21) Appl. No.: 10/907,429

(22) Filed: Mar. 31, 2005

(65) Prior Publication Data

US 2006/0229549 A1    Oct. 12, 2006

(51) Int. Cl.
*A61N 1/30* (2006.01)
*A61K 9/22* (2006.01)

(52) U.S. Cl. ...................... 604/20; 604/890.1
(58) Field of Classification Search ................ 600/396; 604/20, 890.1, 21
See application file for complete search history.

(56) References Cited

U.S. PATENT DOCUMENTS

| | | | |
|---|---|---|---|
| 4,557,723 A | 12/1985 | Sibalis | |
| 4,622,031 A | 11/1986 | Sibalis | |
| 4,640,689 A | 2/1987 | Sibalis | |
| 4,708,716 A | 11/1987 | Sibalis | |
| 4,713,050 A | 12/1987 | Sibalis | |
| 4,919,648 A * | 4/1990 | Sibalis | 604/20 |
| 4,921,475 A | 5/1990 | Sibalis | |
| 4,927,408 A | 5/1990 | Haak et al. | |
| 5,087,240 A | 2/1992 | Sibalis | |
| 5,135,479 A | 8/1992 | Sibalis et al. | |
| 5,224,928 A | 7/1993 | Sibalis et al. | |
| 5,445,606 A * | 8/1995 | Haak et al. | 604/20 |
| 5,591,123 A | 1/1997 | Sibalis et al. | |
| 5,605,536 A | 2/1997 | Sibalis | |
| 5,651,768 A | 7/1997 | Sibalis | |
| 5,865,786 A | 2/1999 | Sibalis et al. | |
| 5,931,804 A | 8/1999 | Sibalis | |
| 5,991,655 A | 11/1999 | Gross et al. | |
| 6,129,696 A | 10/2000 | Sibalis | |
| 6,141,582 A * | 10/2000 | Mori et al. | 604/20 |
| 6,653,014 B2 | 11/2003 | Anderson et al. | |
| 2002/0010415 A1 * | 1/2002 | Simon | 604/20 |
| 2003/0065285 A1 * | 4/2003 | Higuchi | 604/20 |
| 2003/0149393 A1 | 8/2003 | Joshi | |
| 2004/0167460 A1 | 8/2004 | Anderson et al. | |

FOREIGN PATENT DOCUMENTS

| | | |
|---|---|---|
| JP | 54-096076 | 7/1979 |
| JP | 2004 073613 | 3/2004 |

(Continued)

OTHER PUBLICATIONS

Linde, Technical Brief Polymer Thick Film Resistors: Application and Design Criteria, 1997, Microelectronics International vol. 14, Iss. 2; p. 65.*

(Continued)

*Primary Examiner* — Kevin C Sirmons
*Assistant Examiner* — Bradley Osinski
(74) *Attorney, Agent, or Firm* — Ropes & Gray LLP

(57) ABSTRACT

The present invention is directed to a method and apparatus for an electrotherapeutic system including a first and second electrode. Each electrode includes a respective resistance wherein during operation of the electrotherapeutic system, an electrochemical reaction involving one or both of the electrodes varies the respective resistance of at least one of the electrodes.

60 Claims, 4 Drawing Sheets

FOREIGN PATENT DOCUMENTS

| | | |
|---|---|---|
| WO | WO-9630077 A1 | 10/1996 |
| WO | WO-9633771 A2 | 10/1996 |
| WO | WO 99/12606 * | 3/1999 |
| WO | WO-0202182 A2 | 1/2002 |

OTHER PUBLICATIONS 510 (k) Summary by EEMSO, Inc. dated Oct. 14, 2003, 3 pages.

Letter to EEMSO, Inc. from Department of Health & Human Services, dated Oct. 14, 2003, 3 pages.

EEMSO Website Info-1.JPG, http://eemso.com/ESTRIP.cfm, downloaded on Mar. 31, 2005, 1 page.

EEMSO Website Info-2.JPG, http://eemso.com/ESTRIP.cfm, downloaded on Mar. 31, 2005, 1 page.

EEMSO E-Strip Package—Photocopy of a package, Jul. 2003.

European Extended Search Report and European Search Opinion dated Sep. 24, 2009 in International Application No. 06002614.3.

* cited by examiner

APPARATUS FOR ELECTROTHERAPY DRUG DELIVERY WITH ADDED IMPURITIES

TECHNICAL FIELD

The present invention relates to electrotherapeutic devices, and more specifically, to an integrated iontophoretic drug delivery system; for example, iontophoresis and electrophoresis.

BACKGROUND OF THE INVENTION

Because medical equipment contributes significantly to healthcare costs, there is a need for simpler and less costly equipment. The design of earlier drug delivery equipment has several drawbacks. Some notable drawbacks of prior designs are costly and complex equipment manufacturability.

FIG. 1 is a block diagram of a known non-integrated iontophoretic drug delivery system. An electronic controller typically utilizes a microcomputer to control and regulate a drug dose (measured in milliAmp-minutes (mA-min)) to an individual/patient. The electronic controller controls and regulates an electrical current and may utilize LEDs, LCDs, and audio annunciators for user feedback. A pair of electrodes is operably connected to the electronic controller via cable leads. The electronic controller utilizes a current regulator to provide a regulated current for a regulated period as required to provide a regulated dose. The current regulator also limits the current to protect the user/patient. When a finite charge is achieved, e.g., 80 mA-min+/−5%, the current regulator is zeroed and the treatment is completed. At completion, the user turns off the controller and removes the single-use disposable electrodes.

A power source, e.g., 9.0 V alkaline battery, is operably connected to the electronic controller. The controller is typically designed to last for several years and incorporate a power source that is capable of providing power for approximately 40 to 60 treatments before needing to be replaced.

The present invention is provided to address these and other considerations.

SUMMARY OF THE INVENTION

The present invention is directed to a current distribution element of a drug delivery system, e.g., an electrotherapeutic system, including a power source for driving an electrolytic chemical reaction. The current distribution element comprises a first electrode including a resistance and a second electrode including a resistance. A power source connector is operably connected (i.e., coupled) between the first and second electrodes wherein during operation of the electrotherapeutic system, an electrochemical reaction varies the respective resistance of at least one of the electrodes. As such, the current distribution element, namely either or both electrodes, functions as an electrochemical charge controlled rheostat-switch.

Another aspect of the present invention is an electrotherapeutic system comprising a housing and a current distribution element including a first electrode including a resistance and a second electrode including a resistance. The current distribution element is attached to the housing. A power source is operably connected between the first and second electrodes. One of a pair of hydratable matrices is operably attached to each electrode. Each hydratable matrix is capable of containing an ionic solution, e.g., medicament, non-drug electrolyte. During operation of the electrotherapeutic system, an electrochemical reaction involving a portion of the current distribution element in combination with at least one of the pair of hydratable matrices and its respective contents varies the respective resistance of at least one of the first or second electrodes.

Yet another aspect of the present invention is a drug delivery system including a first and second electrode, and a power source connector operably connected between the first and second electrodes. A piece of electrically conductive tape—exclusively conductive in its Z-axis direction—is attached to the power source connector to facilitate connection and retention of a power source, e.g., battery, to the system.

A further aspect of the present invention is a method for delivering a predetermined drug dose. The method includes providing at least one electrode capable of varying its resistance to alter and/or terminate delivery of the drug dose. That is, the electrode functions as an electrochemical charge controlled rheostat-switch such that the resistance of the electrode increases to alter and/or terminate delivery of the drug dose.

An additional aspect of the present invention is a method of manufacturing a current distribution element for an electrotherapeutic system. A power source connector for connecting to a power source is operably coupled to the current distribution element. The current distribution element includes a first electrode connected to a first conductor, and a second electrode connected to a second conductor. The first and second conductors are coupled to the power source connector. The method utilizes a first metallic composition for the first electrode and the first conductor, and a second metallic composition for the second electrode and the second conductor. If desired, the first electrode and the first conductor can be printed simultaneously; and the second electrode and the second conductor can also be printed simultaneously. Additionally, the first and second electrodes can be printed simultaneously.

An object of the present invention is to provide a drug delivery system having comparable control functionality of a more expensive drug delivery system without the need for sophisticated electronic circuitry and associated cables.

Another object of the present invention is to provide a drug delivery system that is significantly simpler and less expensive to manufacture.

A further object of the present invention is to provide a low cost, single use drug delivery system.

A still further object of the present invention is to provide an electrode that functions as both an iontophoretic electrode and as an electrochemical charge controlled rheostat-switch.

Yet another object of the present invention is to provide a method to manufacture a device that includes expected features of common iontophoretic drug delivery systems without the need for an electronic controller, or any other separate control components. Such expected features include at least, total dose regulation and dosing regulation.

Other advantages and aspects of the present invention will become apparent upon reading the following description of the drawings and detailed description of the invention.

DETAILED DESCRIPTION OF THE INVENTION

Figure 1:
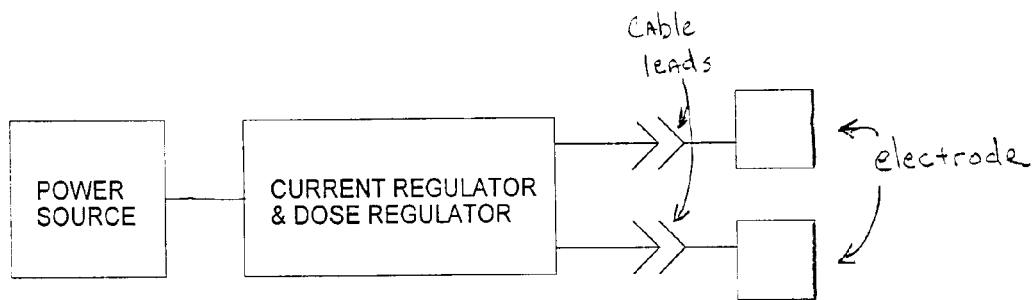
FIG. 1 is a block diagram of a known iontophoretic drug delivery system.

While the present invention is capable of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

The present invention provides comparable control functionality of a more expensive iontophoresis drug delivery system without the need for sophisticated electronic circuitry and associated cables. More specifically, the present invention is directed to an integrated drug delivery system, e.g., electrotherapeutic. The system is fully integrated within a housing. That is, cabling and such is unnecessary because the power source, controller, electrodes, hydratable matrices, etc., are integrated into a single housing. The system includes a current distribution element having the capability of varying its electrical resistance during operation to facilitate delivery of a drug dose. As such, the current distribution element, or a portion thereof, effectively functions as an electrochemical charge controlled rheostat-switch.

Figure 2:
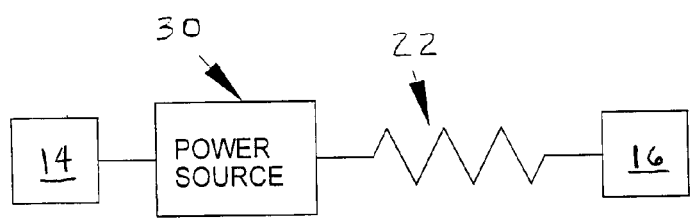
FIG. 2 is a block diagram of one embodiment of the present invention.

A drug delivery system 10 of the present invention shown in FIG. 2 includes a pair of metallic electrodes 14, 16—namely, a first electrode 14 including a resistance, and a second electrode 16 including a resistance. It is to be understood that the electrodes are electric conductors through which an electric current enters or exits an electrochemical half-cell. An electrochemical half-cell may be either an electrolytic half-cell or a galvanic half-cell. A single electrode and its associated ionic solution, e.g., electrolyte, compose one half-cell. Two half-cells—including one positive electrode and one negative electrode—compose one electrochemical cell. For exemplification purposes, the electrodes can be further distinguished as positive 14 (anode) and negative 16 (cathode).

The present invention provides a mechanism whereby one or both of the electrodes 14, 16 are designed to perform the dual functionality of an iontophoretic electrode and an electrochemical charge controlled rheostat-switch, wherein the rheostat-switch function does not interfere with the iontophoretic function of the electrode. In medical applications, the rheostat-switch function does not introduce any detrimental impact on the medical safety and/or medical efficacy of the iontophoretic system.

In one embodiment of the present invention, the positive iontophoretic electrode (i.e., the iontophoretic anode) is designed to additionally function as an electrochemical charge controlled rheostat-switch. The switching function in this embodiment is accomplished via electrochemical electroplating. The electroplated substance is electrically non-conductive, and when the plating reaches a finite thickness—which completely encapsulates the original electrode surface—the iontophoretic current is effectively switched off.

Figure 3:
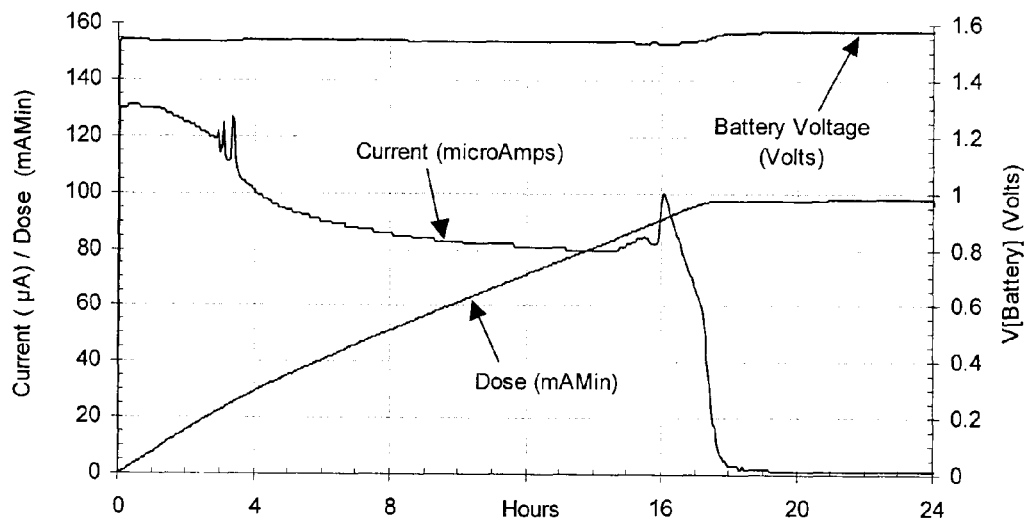
FIG. 3 is a chart of test data of one embodiment of the present invention.

The variance of the resistance of this electrochemical charge controlled rheostat-switch functionality is a function of accumulated charge. Referring to FIG. 3, the basic switch characteristic of the electrochemical charge controlled rheostat-switch functionality is that of a traditional normally closed ON-OFF switch, i.e., a device that provides relatively low electrical resistance when in the ON position (which facilitates the passage of electrical current) and provides relatively high electrical resistance when in the OFF position (which facilitates the blockage of electrical current). It is to be understood that the scope of the present invention is not limited to the basic operation of an ON-OFF switch and can include the variable resistive functionality akin to that of a rheostat, as well as a combination of the two.

As discussed below and shown in FIG. 4, rheostat emulation provides one electrical resistance level until one finite charge level is achieved and a second electrical resistance level after this finite charge level is achieved. This resistive variance provides a first magnitude of electrical current, i.e., a first level of dosing, followed by a different second magnitude of electrical current, i.e., a second level of dosing. In such an embodiment, the chemical properties and/or physical properties of one, or both of the electrochemical half-cells—comprising the electrode and associated electrolyte—is configured to facilitate the desired rheostat functionality.

Referring again to FIG. 2, a current regulator 22 (and a current limiter) may be operably connected to one or both of the electrodes 14, 16. A simplistic regulator 22 in the form of a resistor component may be utilized as an example of a low-cost implementation. The power source of the drug delivery system 10 may be an electrochemical source such as a primary battery or a series of batteries. Alternatively, the power source may be an electrical generator and/or electrostatic storage device such as a capacitor or bank of capacitors. In one embodiment, the current regulator 22 is utilized to regulate electrical current as well as to provide current limitation. The current regulator 22 may be connected to either electrode 14, 16.

The electrochemical charge controlled rheostat-switch functionality is an inherent part of the current distribution element 12. Namely, one or both electrodes 14, 16 includes a metallic chemical composition capable of operable cooperation with an electrolyte solution—either the positive or negative electrolyte of the associated electrode. One of a pair of hydratable matrices 28, 29 is operably connected to each electrode 14, 16. Each hydratable matrix 28, 29 is associated with an electrode, 14 16, i.e., the iontophoretic anode (positive electrode) and the iontophoretic cathode (negative electrode), respectively. Depending on the electrochemical activity during iontophoresis, a matrix pH buffer may or may not be required.

The drug delivery system 10 of the present invention can be operably configured dependent upon the polarity of the drug to be delivered. That is, if the administered drug is formulated as a positive ionic medicament(s), then the electrode connected to the positive side of the power source is considered the drug delivery electrode; and the electrode connected to the negative side of the power source is considered the return electrode. And conversely, if the drug to be delivered is formulated as a negative ionic medicament(s), then the electrode connected to the negative side of the power source is the drug delivery electrode; and the electrode connected to the positive side of the power source is the return electrode. In the case where both positively and negatively charged drugs are to be delivered simultaneously, both electrodes function simultaneously as the drug delivery and return electrodes.

In a single positive polarity ionic drug delivery application, the hydratable matrix associated with the drug delivery electrode contains the ionic medicament; and the hydratable matrix associated with the return electrode contains the non-drug ionic electrolyte. That is, if a positive drug is to be iontophoretically delivered, the anode matrix is the drug delivery electrode matrix; otherwise it is the return electrode matrix. And if a negative drug is to be iontophoretically delivered, then the cathode electrode matrix is the drug delivery matrix, otherwise it is the return electrode matrix.

For example, a common iontophoretically delivered drug is Dexamethasone Sodium Phosphate ("Dex"). This ionic drug medicament has a negative polarity and if Dex is used with the embodiment shown in FIG. 2, then ionic drug medicament is placed in the negative electrode's 16 associated matrix (not shown)—often referred to as the cathode reservoir matrix, cathode matrix, or anionic matrix; and a non-drug ionic solution (i.e., effectively inert ionic solution) is placed in the positive electrode's 14 associated matrix (not shown)—often referred to as the anode reservoir matrix, anode matrix, or cationic matrix.

During iontophoresis, a chemical change occurs at one or both of the electrodes 14, 16 due to the flow of electrical current and the chemical composition of the each electrode and its associated electrolyte, which results in the variation (e.g., increase) in resistance of the respective electrodes as a function of the accumulated charge. This increase in resistance will ultimately zero the electrical current in the electrotherapeutic device.

One or both of the iontophoretic electrodes 14, 16 facilitate the electrochemical reaction during iontophoresis. The electrochemical reaction at one electrode, i.e., at one half-cell, may be oxidation while the reaction at other electrode may be reduction. The electrochemical reaction can be designed to facilitate a variance in electrical resistance. This variance in resistance can be the result of an additive process such as electroplating, or a subtractive process such as electroetching.

In FIG. 2, the electrochemical charge controlled rheostat-switch functionality is inherent in the composition of at least a portion of the current distribution element 12 associated with the return electrode 14. The metal utilized for the return electrode 14 is Ag (silver). The electrolyte utilized for operable cooperation with the return electrode 14 is a medical grade saline solution (e.g., sodium chloride solution, 0.9%) and is a common non-drug electrolyte employed in an iontophoretic return electrode hydratable matrix. During iontophoresis, oxidation reactions occur at the return electrode 14. The primary chemical reaction plates the Ag of the return electrode 14 with a AgCl surface layer. The plating increases the resistance of the return electrode 14 and after a finite charge is achieved, the resistance increases rapidly and significantly, thereby terminating the flow of iontophoretic current, i.e., terminating the dosing after the final desired dose is achieved.

FIG. 3 displays test results of one embodiment of the present invention showing the relationship between the voltage potential of the power source, i.e., battery, the iontophoretic current (measured in microAmps), and the dose, i.e., charge (measured in milliAmp-minutes). Note that milliAmp-minutes is a measurement of charge, and charge is the first integral of current with respect to time. A test load resistor of 5 kOhms is operably connected to one of the electrodes 14, 16. The value of 5 kOhms is chosen to represent a minimal skin-body resistance. The observed battery voltage is relatively constant at approximately 1.55 Volts. The battery voltage increases slightly when the resistance of the electrode functioning as the electrochemical charge controlled rheostat-switch increases significantly; that is, when the current is terminated at dose completion. The slight rise of battery voltage is typical and is due to the "unloading" of the battery.

The actual in vivo current profile will vary depending upon where the device 10 is placed on the human body due to different body sites having different resistances. For a constant load resistance, FIG. 3 indicates that the drug delivery system 10 of the present invention will supply relative constant current until the resistance at the specified electrode increases to stop the current at completion of the dose delivery.

During a typical iontophoretic treatment, body resistance will vary and therefore the current will vary proportionally. One advantage of the present invention is that the increasing resistance of the electrode terminates the dose as a function of actual accumulated dose, and therefore the operation is independent of time and skin resistance.

The charge required to plate the electrode with the required high-resistance layer—which may be a series of minute layers—is dependent on several factors, e.g., electrolyte formulation, Ag ink formulation, ink thickness or amount of layers deposited, and the area to which ink is applied. If the required minimal depth of Ag ink (Ag particles within a binder solution) is utilized, the charge is relatively independent of ink depth. As such, the desired final dose, i.e., the maximum allowable charge, will be a function of other variables, e.g., area, ink formulation, etc. It is to be understood that the present invention is not limited to the use of an ink or similar solution to construct the electrodes 14, 16 of the current distribution element. Therefore, a film or sheet of Ag could be utilized instead of Ag ink.

Referring again to FIG. 3, the electrical characteristics are shown for an embodiment of the present invention designed to provide a dosage of 100+/−15 mA-min (which guarantees a dose of at least 80 mA-min). The dose accuracy of this embodiment is less than that of one utilizing a more expensive and sophisticated electronic controller, but is suitable for a low-cost disposable drug delivery system. It can be seen from FIG. 3 that at about seventeen hours, the electrode is completely plated and the resistance increases significantly, which terminates the treatment at approximately 98 mA-min.

The primary electrochemical reaction, i.e., primary electrolytic reaction or primary oxidation reaction, that occurs at the return electrode 14 of the current distribution element 12 for this exemplification is $Ag+Cl^- \rightarrow AgCl+e^-$. The electron "e" is required for the flow of electrical current. The AgCl forms a layer on top of the Ag ink. AgCl, unlike Ag, is non-conductive. The accumulation or layering of AgCl provides the required high resistance to terminate the iontophoretic current and thereby terminate the iontophoretic dosing; thus providing the electrical open-switch functionality after the predetermined dose is accumulated.

When utilizing a simple and low cost resistor as the current regulator 22, the value of the resistor is dependent upon the battery supply voltage, maximum required current, and the application. The current regulator 22 also functions as a current limiter. The current limit for the illustrated embodiment is 300 microamperes—that is, the maximum nominal voltage of about 1.5 V is divided by the absolute minimum load resistance of zero (0) Ohms in series with the current limiting resistor of 5 kOhms to equal 300 µA. The current limit protects against harm to the patient should the iontophoretic device be placed on damaged or broken skin wherein the skin resistance is relatively small. This concern is more critical for devices utilizing higher voltage power supplies, e.g., a 6 or 12 Volt system employing a series of multiple lithium battery cells.

The table below illustrates the characteristics of the simple current regulator 22 employing a 5 kOhm resistor with a 1.5 Volt power source. This configuration is satisfactory for low cost applications, but is inferior to an electronic semiconductor current regulator. For a 500% variance in resistance, the variance in current is reduced from 500% to 67%.

TABLE 1

| Skin-Body Resistance (Ohms) | Current with Regulation (microAmps) | Current without Regulation (microAmps) |
| --- | --- | --- |
| 5,000 | 150 | 300 |
| 1,000 | 250 | 1,500 |
| 500% Variance | 67% Variance | 500% Variance |

Although this embodiment utilizes a resistor, it is to be understood that the present invention is not limited to incorporating such a component. As such, an electronic semiconductor current regulator may be implemented for applications requiring a more finite current and/or for applications requiring a more finite dosing period (because variance in current results in a proportional variance in dosing period for the finite dose set by the composition of the conductive distribution element).

In addition, the composition of either or both electrodes 14, 16 of the current distribution element 12 can be configured to facilitate differing resistance profiles, which further facilitates differing current profiles, which still further facilitates varying dosage profiles. Varying the physical and/or chemical properties of the electrodes 14, 16 and/or the electrolyte within their respective associated matrices 28, 29 will facilitate the required variances in current and/or dosing profiles.

Figure 4:
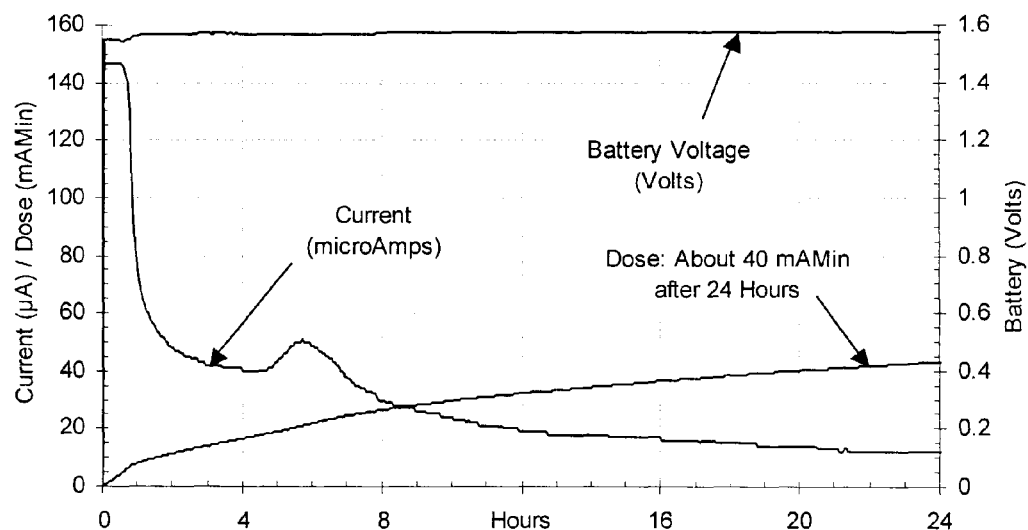
FIG. 4 is a chart of test data of another embodiment of the present invention.

A second current profile shown in FIG. 4 is typical for a treatment regimen requiring an initial bolus excitation followed by low-level baseline excitation. The graph of FIG. 4 illustrates a modified current profile that was obtained by adding impurities to 75% of the surface area of the return electrode employed in the device having electrical characteristics shown in FIG. 3. Comparing the current profile of the modified return electrode of FIG. 4 to the unmodified return electrode of FIG. 3, the unmodified embodiment yields a relatively high current for approximately seventeen hours and then approximately zero current thereafter; and the modified embodiment of FIG. 4 yields a high current for approximately one hour followed by a low current the remaining twenty-three hours. Comparison of FIGS. 3 and 4 exemplify the difference between the ON-OFF switch and rheostat (multi-level) functionality of the present invention.

Figure 5:
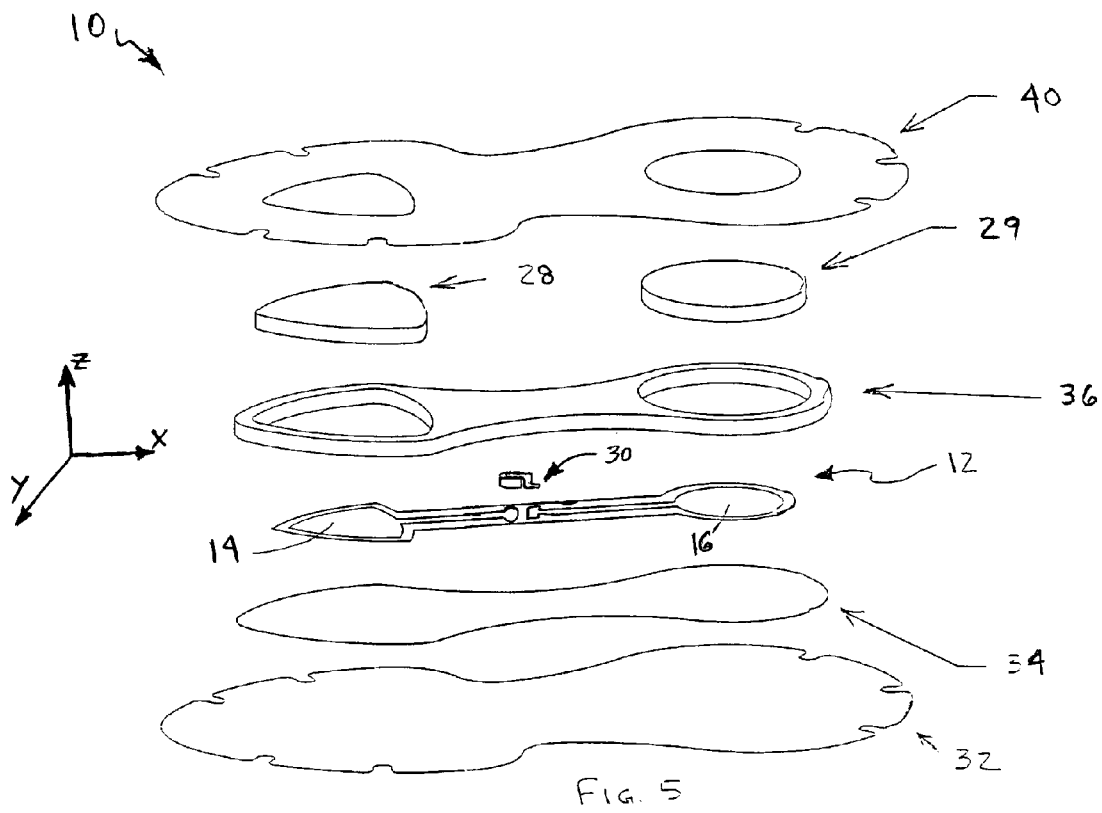
FIG. 5 is an exploded perspective view of one embodiment of the present invention.

Referring now to FIG. 5, another embodiment of the present invention is depicted. Depending on the application and duration of treatment, the drug delivery system 10 may include a breathable or non-breathable skin fixation material 32. An adhesive is located on one side of the skin fixation material 32 and faces toward a single coated medical pressure sensitive polypropylene film 34 to provide adhesion to it. The perimeter of the skin fixation material 32 is greater than that of the single coated medical pressure sensitive polypropylene film 34. The additional area outside the perimeter of the single coated medical pressure sensitive polypropylene film 34 includes the adhesive that contacts the skin. The single coated medical pressure sensitive polypropylene film 34 is coated on one side and holds the iontophoretic current distribution element 12. That is, the area inside the perimeter of the single coated medical pressure sensitive polypropylene film 34 houses the electrical and electrochemical components that are attached to, or integral with, the current distribution element 12.

The single coated medical pressure sensitive polypropylene film 34 provides a moisture barrier and prevents unwanted moisture (e.g., shower water) from entering into the device through the skin fixation material 32. The polypropylene film 34 also prevents moisture (i.e., the electrolyte added to the two hydrated matrices) from escaping from the device 10 through the skin fixation material 32; thus permitting the use of a "breathable" skin fixation material. In short term treatment applications wherein a "non-breathable" skin fixation material 32 provides a moisture barrier, the single coated medical pressure sensitive polypropylene film 34 may be eliminated to reduce the cost of manufacturing.

The adhesive side of the medical pressure sensitive polypropylene film 34 faces toward the current distribution element 12, polyethylene foam pad 36, and the pair of matrices 28, 29. The perimeter of the electrodes 14, 16 is significantly less than that of the hydratable matrices 28, 29. Thus, the single coated medical pressure sensitive polypropylene film 34 is adhered to the pair of matrices 28, 29 in the area of the electrodes 14, 16 that extends beyond the perimeter of the current distribution element 12. The single coated medical pressure sensitive polypropylene film 34 is also adhered to the current distribution element 12 and a polyethylene foam pad 36.

The polyethylene foam pad 36 with adhesive on both layers is attached to the pressure sensitive polypropylene film 34 and provides multiple functions. The polyethylene foam pad 36, or equivalent, provides the required lateral moisture barrier (i.e., in the X and Y axes) surrounding both matrices 28, 29. As such the polyethylene foam pad 36 is relatively thick in the Z-axis. Utilization of a foam material provides the required thickness without sacrificing the needed flexibility. Note that the polyethylene foam pad 36 is adhered to the single coated medical pressure sensitive polypropylene film 34 via the adhesive provided by both materials. This strong double adhesion provides a relatively strong seal around each electrode 14, 16 and each matrix 28, 29. This feature reduces or prevents leakage of the electrolyte from the matrices 28, 29 into the electrical component cavity; and also prevents electrolyte leakage from one electrode to the other electrode.

The adhesive material on the bottom side of the polyethylene foam pad 36 provides adhesion to the topside of the current distribution element 12 and the components attached to the topside of the current distribution element. This provides the top-level moisture-barrier seal for the electrical circuitry, e.g., power source, power source connector 30, and current regulator.

A release liner 40 is held in place by the adhesion provided by the skin fixation material 32 and the polyethylene foam pad 36. The release liner 40 protects the skin fixation adhesive 32 and the polyethylene foam pad 36 until the device 10 is ready for use, at which point in time the release liner 40 is typically removed just after the matrices 28, 29 are hydrated and just prior to applying the device to the skin. The openings in the release liner 40 facilitate the hydration of the matrices 28, 29 without the need to remove the release liner.

Figure 6:
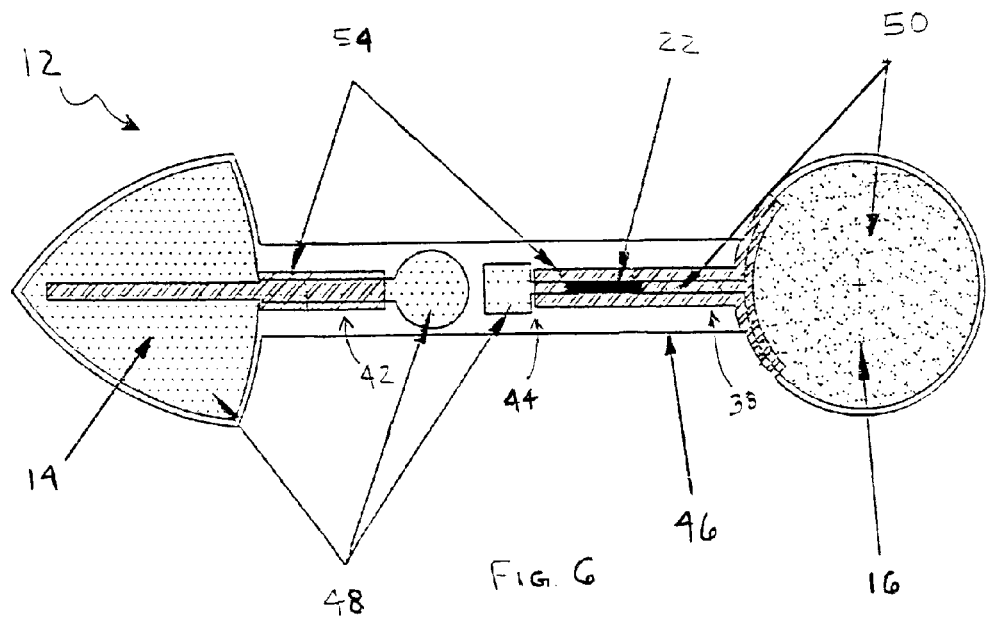
FIG. 6 is a top view of one embodiment of the present invention.

One embodiment of printed current distribution element 12 is illustrated in FIG. 6. A substrate 46 for the current distribution element 12 is a polyester film, or an equivalent, e.g., an electrically non-conductive thin flexible substrate. Electrically conductive metal inks compose first 38, second 42, and third 44 conductors. Ag/AgCl ink 50 is deposited to fabricate the electrolytic iontophoretic cathode 16 and the first conductor 38. Ag ink 48 is deposited to fabricate an electrolytic iontophoretic anode 14 and another two conductors 42, 44.

An electrically resistive material such as carbon ink is deposited on the substrate 46 to fabricate an electrical resistor 22 in series with the first 38 and third 44 conductors, iontophoretic cathode 16, and the power source connector 30. The carbon ink resistor 22 is printed in a manner similar to that used for printing the metallic inks. The resistor 22 provides current regulation and current limit. It is to be understood that the present invention is not limited to this simple current regulator; and that it can incorporate a more sophisticated and precise current regulator and/or current limiter, or none at all. In addition, a dielectric ink 54 may be printed over certain sections of the electrically conductive metal inks intended to function as insulated conductors.

The embodiment shown in FIG. 6 may utilize the same metal inks for both the cathode 16 and anode 14 that can also be used for the first 38 and third conductors 44 (as well as second conductor 42) respectively. Utilizing a single metal ink eliminates the need for a separate deposition of multiple metal inks to fabricate conductors and/or electrodes of existing flexible devices. The present invention eliminates the need for separate metal ink depositions to fabricate separate conductors, thereby lowering manufacturing cost and enhancing reliability by reducing components, reducing manufacturing steps, and reducing the number of resultant physical/electrical interconnections.

Furthermore, the metal inks employed to fabricate the electrodes 14, 16 of the present invention are not limited to Ag and Ag/AgCl. For example, one metal, e.g., Ag, may be utilized for both electrodes 14, 16. The exclusive use of Ag reduces the cost of manufacturing by employing only one metallic ink deposition to fabricate the two electrodes 14, 16 and all of the separate interconnecting conductors. The exclusive use of Ag does have one drawback in comparison to the Ag and Ag/AgCl embodiment presented herein—namely, the voltage required for reduction at the iontophoretic cathode is greater. As such, the exclusive use of Ag requires a higher voltage power supply, e.g., a series of batteries as opposed to the single battery. Therefore, such tradeoffs should be considered when altering the materials used for the electrodes and/or electrolytes.

Figure 7:
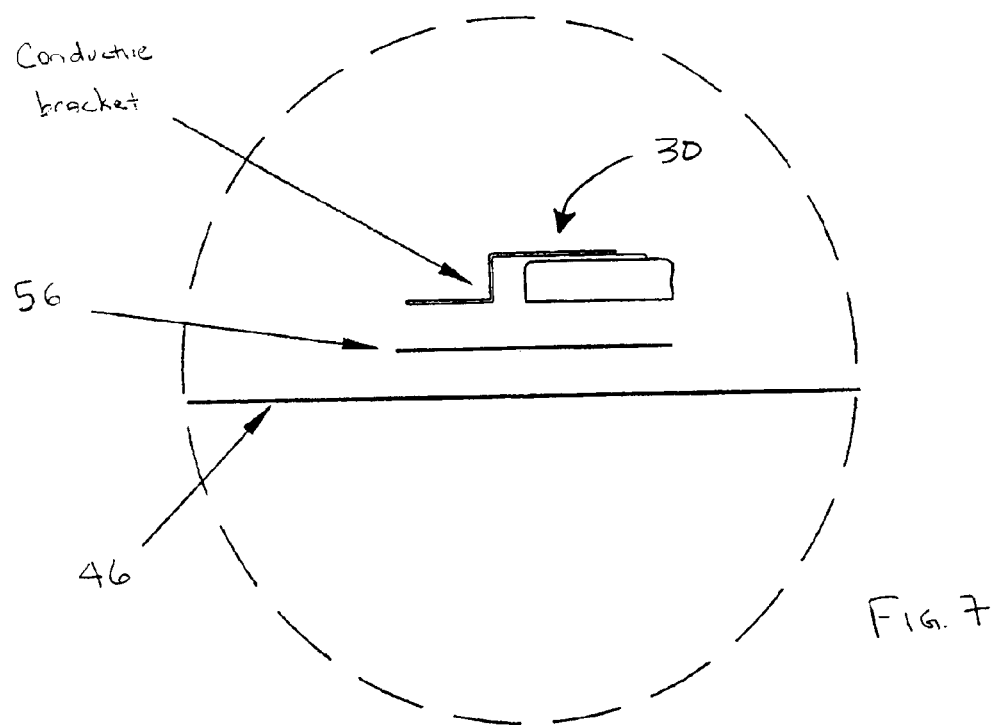
FIG. 7 is a side view of one embodiment of the present invention utilizing a Z-axis conductive tape; and, FIG. 8 is a top view of the embodiment of the present invention shown in FIG. 7.
Figure 8:
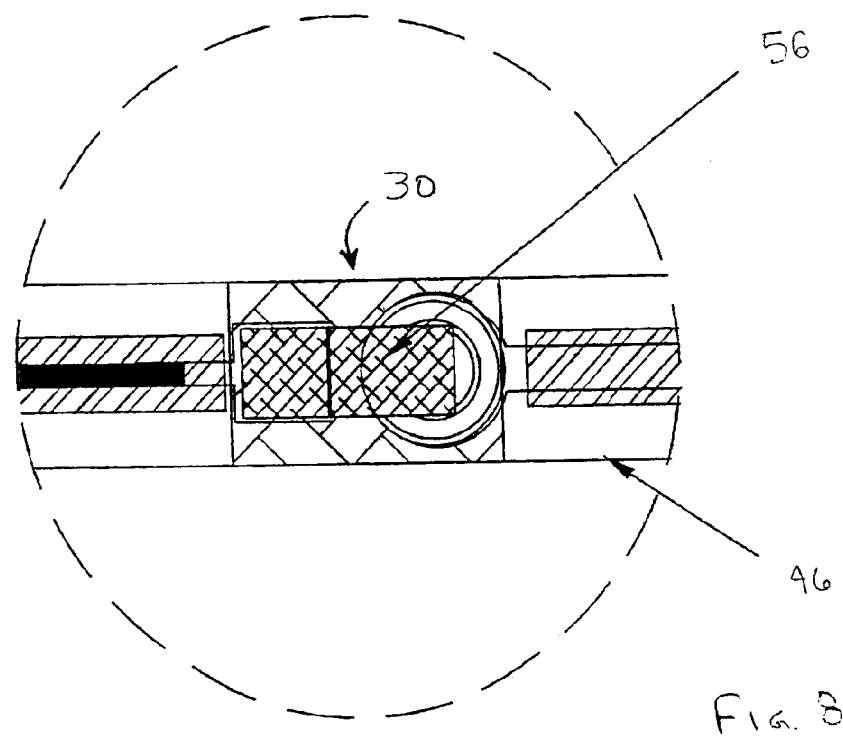

FIGS. 7 and 8 illustrate a further embodiment of the present invention directed to the connection of the power source with the current distribution element 12. The power source in the illustrated embodiment is a tabbed button battery. It is to be understood that the present invention is not limited to this type of power source and may include among other embodiments, such as a connected series of multiple cells. The multiple cell embodiment provides a higher voltage potential as required to drive higher resistance skin and/or provide iontophoresis of a finite dose in a shorter period of time by providing higher current for a given skin resistance.

An electrically conductive tape 56 exclusively conductive in its Z-axis (e.g., 3M™ Electrically Conductive Tape 9703) is used to adhere and electrically connect the battery 30 to the conductors of the current distribution element 12. This tape is applicable for interconnection of silver ink/polyester based flexible circuits and provides stable electrical performance at moderately high temperatures with good adhesion to metallic and other commonly used surfaces, including: polyimide and polyester flex circuit materials, FR-4 board, copper, steel, and aluminum. The Z-axis conductive tape is an isotropic, electrically conductive, pressure sensitive adhesive (PSA) transfer tape. It is tacky and consists of a PSA matrix with conductive particles. These particles allow electrical conduction through the adhesive thickness (Z-axis), but not in the plane of the tape. The PSA properties of the Z-axis tape make it easy to handle and apply without need for thermal bonding. This single-axis conduction feature allows one contiguous segment of Z-axis tape 56 to be used to simultaneously connect both the battery anode and battery cathode of the embodiment illustrated in FIG. 7.

At a minimum, implementation of the Z-axis tape: eliminates the need for two separate applications of a conductive adhesive at the battery anode tab and battery cathode tab of the battery; eliminates the need to maintain an insulation barrier between the battery anode tab connection and battery cathode tab connection; provides suitable mechanical adhesion in addition to the required electrical connections; eliminates the need for curing as required with metallized electrically conductive inks or electrically conductive paste type adhesives; decreases the probability of connection failure, e.g., the cracking of electrically conductive paste type adhesives when employed on a flexible substrate; and, is simpler to apply than electrically conductive paste type adhesives.

While specific embodiments of the present invention have been illustrated and described, numerous modifications come to mind without significantly departing from the spirit of the invention, and the scope of protection is only limited by the scope of the accompanying claims.

What is claimed is:

1. A current distribution element for an electrotherapeutic system including a power source for driving an electrolytic chemical reaction and facilitating delivery of a drug dose, the current distribution element comprising:
    a first electrode including a first material having a resistance, and configured to deliver a drug dose; and
    a second electrode including a second material having a resistance, and configured to return current to the power source;
    wherein current is delivered from the first electrode to the second electrode, thereby delivering the drug dose and causing electroplating on the second electrode with a nonconductive substance formed from the second material wherein impurities added to the second material facilitate electroplating on the second electrode, thereby varying the resistance over time in accordance with a predetermined resistance profile.

2. The current distribution element of claim 1 further comprising:
    a power source connector being operably connected between the first and second electrodes;
    a first terminal being operably connected to the power source connector;
    a second terminal being operably connected to the power source connector;
    a first conductor being operably connected between the first terminal and the first electrode; and,
    a second conductor being operably connected between the second terminal and the second electrode.

3. The current distribution element of claim 2 wherein the first conductor and the first electrode comprise the same metal composition.

4. The current distribution element of claim 3 wherein the metal composition comprises Ag.

5. The current distribution element of claim 3 wherein the metal composition comprises Ag/AgCl.

6. The current distribution element of claim 2 wherein the second conductor and the second electrode comprise the same metal composition.

7. The current distribution element of claim 6 wherein the metal composition comprises Ag.

8. The current distribution element of claim 6 wherein the metal composition comprises Ag/AgCl.

9. The current distribution element of claim 2 wherein the first conductor, the first electrode, the second conductor, and the second electrode comprise the same metal composition.

10. The current distribution element of claim 9 wherein the metal composition comprises Ag.

11. The current distribution element of claim 9 wherein the metal composition comprises Ag/AgCl.

12. The current distribution element of claim 2 further comprising:
a current regulator being operably connected between the power source connector and either the first or second electrode.

13. The current distribution element of claim 12 wherein the current regulator is a resistor.

14. The current distribution element of claim 13 wherein the resistor is printed.

15. The current distribution element of claim 13 wherein the resistor is a discrete component.

16. The current distribution element of claim 13 wherein the value of the resistor being selected in response to power source voltage, maximum required current, or the application of the electrotherapeutic system.

17. The current distribution element of claim 1 further comprising:
a first hydratable matrix being operably attached to the first electrode; and,
a second hydratable matrix being operably attached to the second electrode.

18. The current distribution element of claim 17 wherein either the first or second hydratable matrix includes an ionic medicament.

19. The current distribution element of claim 17 wherein either the first or second hydratable matrix includes a non-drug ionic electrolyte.

20. The current distribution element of claim 17, wherein a solution in at least one of the first and second hydratable matrices undergoes a chemical reaction with a metal in at least one of the first and second electrode thereby varying the resistance of said electrode.

21. The current distribution element of claim 17, wherein the second hydratable matrix includes an electrolyte, and wherein the properties of the second electrode and the properties of the electrolyte are configured to produce a chemical reaction which controls delivery of the drug to deliver a pre-determined dose.

22. The current distribution element of claim 1 wherein the power source is a battery.

23. The current distribution element of claim 1 wherein the power source is an electrochemical storage device.

24. The current distribution element of claim 1 wherein the power source includes an electrical generator and/or an electrostatic storage device.

25. The current distribution element of claim 1 further comprising a means for varying the resistance of the first electrode and/or the second electrode.

26. The current distribution element of claim 1, wherein the electroplating process terminates the drug dose delivered by the first electrode.

27. The current distribution element of claim 1, wherein the impurities are added to the surface area of the electrode.

28. The current distribution element of claim 1, wherein the electroplating causes termination of the current.

29. The current distribution element of claim 28, wherein the current is terminated once the final desired drug dose is achieved.

30. An electrotherapeutic system comprising:
a housing;
a current distribution element including a first electrode including a first material having a resistance, and configured to deliver a drug dose and a second electrode including a second material having a resistance, the current distribution element being attached to the housing,
a power source being operably connected between the first and second electrodes, wherein the second electrode is configured to return current to the power source;
a first hydratable matrix being operably attached to the first electrode, the first hydratable matrix containing a first ionic solution;
a second hydratable matrix being operably attached to the second electrode, the second hydratable matrix containing a second ionic solution,
wherein current is delivered from the first electrode to the second electrode, thereby delivering the drug dose and, wherein interaction of the second hydratable matrix with the second electrode causes electroplating on the second electrode with a nonconductive substance formed from the second material, wherein a composition of the second hydratable matrix is configured to facilitate the electroplating thereby varying a resistance over time in accordance with a predetermined resistance profile.

31. The electrotherapeutic system of claim 30 further comprising:
a first conductor being operably connected between the power source and the first electrode; and,
a second conductor being operably connected between the power source and the second electrode.

32. The electrotherapeutic system of claim 31 wherein the first conductor and the first electrode comprise the same metal composition.

33. The electrotherapeutic system of claim 32 wherein the metal composition comprises Ag.

34. The electrotherapeutic system of claim 32 wherein the metal composition comprises Ag/AgCl.

35. The electrotherapeutic system of claim 31 wherein the second conductor and the second electrode comprise the same metal composition.

36. The electrotherapeutic system of claim 35 wherein the metal composition comprises Ag.

37. The electrotherapeutic system of claim 35 wherein the metal composition comprises Ag/AgCl.

38. The electrotherapeutic system of claim 31 wherein the first conductor, the first electrode, the second conductor, and the second electrode comprise the same metal composition.

39. The electrotherapeutic system of claim 38 wherein the metal composition comprises Ag.

40. The electrotherapeutic system of claim 38 wherein the metal composition comprises Ag/AgCl.

41. The electrotherapeutic system of claim 30 wherein the power source is a battery.

42. The electrotherapeutic system of claim 30 wherein the power source is an electrochemical storage device.

43. The electrotherapeutic system of claim 30 wherein the power source is an electrical generator and/or an electrostatic storage device.

44. The electrotherapeutic system of claim 30 further comprising:
a current regulator being operably connected between the power source and either the first or second electrode.

45. The electrotherapeutic system of claim 44 wherein the current regulator is a resistor.

46. The electrotherapeutic system of claim 45 wherein the resistor is printed.

47. The electrotherapeutic system of claim 45 wherein the resistor is a discrete component.

48. The electrotherapeutic system of claim 45 wherein the value of the resistor being selected in response to power source voltage, maximum required current, or the application of the electrotherapeutic system.

49. The electrotherapeutic system of claim 30 further comprising a means for varying the resistance of the first electrode and/or the second electrode.

50. The electrotherapeutic system of claim 30 wherein the housing includes an adhesive for facilitating attachment to a body.

51. The electrotherapeutic system of claim 30 wherein the first ionic solution and the second ionic solution are identical.

52. The electrotherapeutic system of claim 30 wherein the first ionic solution includes a medicament.

53. The electrotherapeutic system of claim 30 wherein the first ionic solution includes a non-drug electrolyte.

54. The electrotherapeutic system of claim 30, wherein the electroplating causes termination of the current.

55. The electrotherapeutic system of claim 54, wherein the current is terminated once the final desired drug dose is achieved.

56. A current distribution element for an electrotherapeutic system including a power source for driving an electrolytic chemical reaction, the current distribution element comprising:
   a first electrode including a first material having a resistance;
   a second electrode including a second material having a resistance; and,
   a power source connector being operably connected between the first and second electrodes, wherein during operation of the electrotherapeutic system, an electrochemical reaction causes electroplating on the second electrode with a nonconductive substance formed from the second material wherein impurities added to the second material facilitate electroplating on the second material, thereby varying the resistance over time in accordance with a predetermined resistance profile.

57. The current distribution element of claim 56, wherein the impurities are added to the surface area of the electrode.

58. The current distribution element of claim 56, wherein the electroplating causes termination of the current.

59. An electrotherapeutic system comprising:
   a housing;
   a current distribution element including a first electrode including a first material having a resistance, and a second electrode including a second material having a resistance, the current distribution element being attached to the housing;
   a power source being operably connected between the first and second electrodes;
   a first hydratable matrix being operably attached to the first electrode, the first hydratable matrix containing a first ionic solution;
   a second hydratable matrix being operably attached to the second electrode, the second hydratable matrix containing a second ionic solution;
   wherein during operation of the electrotherapeutic system, an electrochemical reaction involving a portion of the current distribution element in combination with the second hydratable matrix and its respective ionic solution causes electroplating on the second electrode with a nonconductive substance formed from the second material, wherein a composition on the second hydratable matrix is configured to facilitate the electroplating thereby varying a resistance over time in accordance with a predetermined resistance profile.

60. The electrotherapeutic system of claim 59, wherein the electroplating causes termination of the current.

* * * * *

UNITED STATES PATENT AND TRADEMARK OFFICE
CERTIFICATE OF CORRECTION

| | | |
|---|---|---|
| PATENT NO. | : 8,386,029 B2 | Page 1 of 1 |
| APPLICATION NO. | : 10/907429 | |
| DATED | : February 26, 2013 | |
| INVENTOR(S) | : Hause, Jr. et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 742 days.

Signed and Sealed this
Eighteenth Day of November, 2014

Michelle K. Lee
*Deputy Director of the United States Patent and Trademark Office*